US007986342B2

(12) United States Patent
Yogesan et al.

(10) Patent No.: US 7,986,342 B2
(45) Date of Patent: Jul. 26, 2011

(54) MULTI-PURPOSE IMAGING APPARATUS AND ADAPTORS THEREFOR

(75) Inventors: Kanagasingam Yogesan, Perth (AU); Ian Constable, Perth (AU); Gabriel Suplewski, Perth (AU); Jean-Pierre Guillon, Perth (AU)

(73) Assignee: The Lions Eye Institute Limited, Perth (AU)

( * ) Notice: Subject to any disclaimer, the term of this patent is extended or adjusted under 35 U.S.C. 154(b) by 1134 days.

(21) Appl. No.: 10/983,785

(22) Filed: Nov. 8, 2004

(65) Prior Publication Data

US 2005/0200707 A1    Sep. 15, 2005

Related U.S. Application Data

(63) Continuation-in-part of application No. PCT/AU03/00564, filed on May 8, 2003.

(30) Foreign Application Priority Data

Aug. 5, 2002 (AU) .......................................... PS2190

(51) Int. Cl.
*H04N 5/225* (2006.01)
*H04N 9/04* (2006.01)
(52) U.S. Cl. ......... 348/207.99; 348/75; 348/66; 348/78; 348/67; 348/68; 348/69; 348/72; 600/101
(58) Field of Classification Search .................... 348/75, 348/78, 72, 66–69, 207.99; 600/172, 101
See application file for complete search history.

(56) References Cited

U.S. PATENT DOCUMENTS

| 3,169,459 | A | | 2/1965 | Friedberg et al. |
| 5,239,984 | A | | 8/1993 | Cane et al. |
| 5,512,740 | A | * | 4/1996 | Hone et al. ............... 235/462.45 |
| 5,682,199 | A | * | 10/1997 | Lankford ........................ 348/72 |
| 5,743,731 | A | | 4/1998 | Lares et al. |
| 5,885,214 | A | | 3/1999 | Monroe et al. |
| 6,106,457 | A | * | 8/2000 | Perkins et al. ................. 600/175 |
| 6,159,189 | A | | 12/2000 | Finnemore et al. |
| 6,168,274 | B1 | | 1/2001 | Matthews |
| 6,283,596 | B1 | | 9/2001 | Yoshimura |
| 6,393,431 | B1 | | 5/2002 | Salvati et al. |
| 6,474,815 | B1 | | 11/2002 | Ulbers et al. |
| 7,371,209 | B2 | * | 5/2008 | Viebach et al. ............... 600/102 |
| 7,624,924 | B2 | * | 12/2009 | Byun et al. ............... 235/462.01 |
| 2002/0042039 | A1 | | 4/2002 | Kim et al. |
| 2003/0123028 | A1 | * | 7/2003 | Yogesan et al. ............... 351/214 |
| 2005/0041207 | A1 | * | 2/2005 | Miller et al. ................... 351/200 |

FOREIGN PATENT DOCUMENTS

DE    200 19 803    2/2001

(Continued)

*Primary Examiner* — Nicholas G Giles
*Assistant Examiner* — Antoinette T Spinks
(74) *Attorney, Agent, or Firm* — Vedder Price P.C.; Thomas J. Kowalski; Heidi Lunasin

(57) ABSTRACT

Provided is a multi-purpose imaging apparatus (10) comprising a body (14) and imaging means (36) housed within the body (14). The body (14) is adapted to releasably engage an adaptor (12). The adaptor (12) has an aperture (108) extending therethrough that aligns with the optical axis (X) of the imaging means (36) when so engaged, such that at least a portion of the optical axis (X) is not obscured. The adaptor (12) also has optics for illuminating a subject within the optical axis (X) for diagnostic purposes.

49 Claims, 13 Drawing Sheets

FOREIGN PATENT DOCUMENTS

| | | |
|---|---|---|
| DE | 100 64 544 | 6/2002 |
| EP | 0274038 | 7/1988 |
| EP | 0 691 103 | 1/1996 |
| EP | 0 916 306 | 5/1999 |
| GB | 2 123 977 | 2/1984 |
| GB | 2 359 375 | 8/2001 |
| JP | 59221080 A * | 12/1984 |
| JP | 10 210328 | 8/1998 |
| JP | 11155815 | 6/1999 |
| WO | WO 97/36537 | 10/1997 |
| WO | WO 99/29229 | 6/1999 |
| WO | WO 01/89375 | 11/2001 |
| WO | WO 0189375 A1 * | 11/2001 |

* cited by examiner

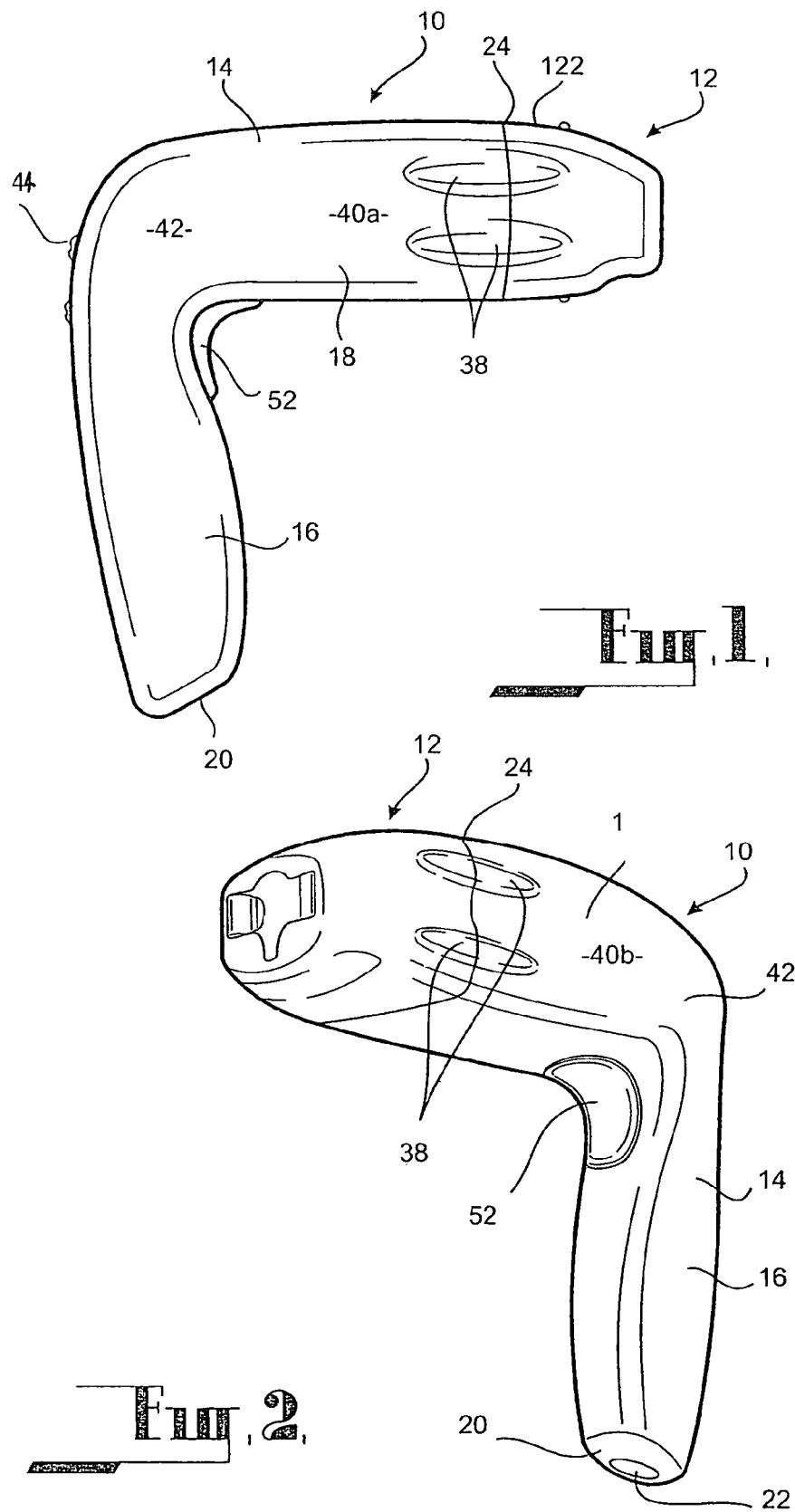

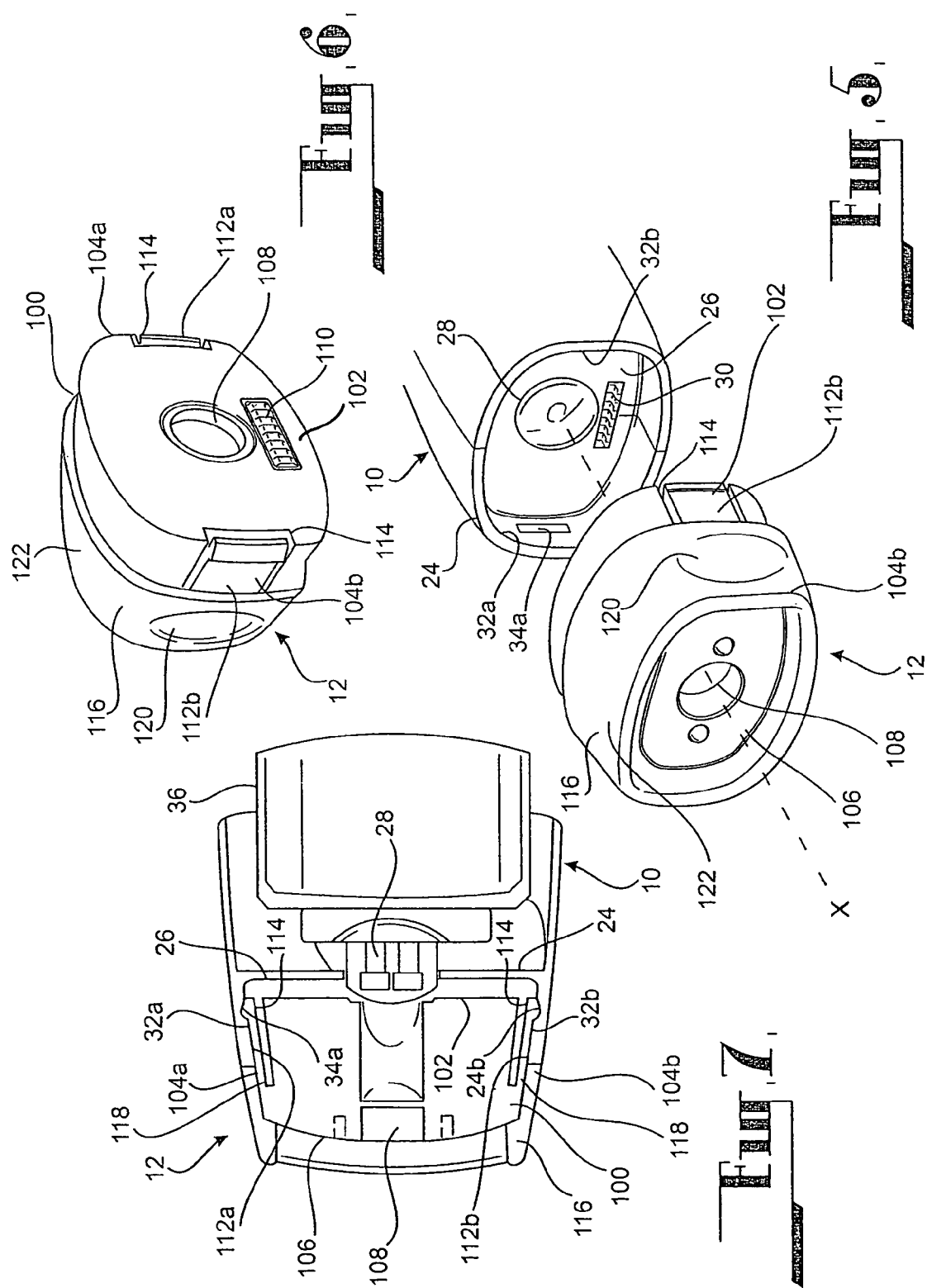

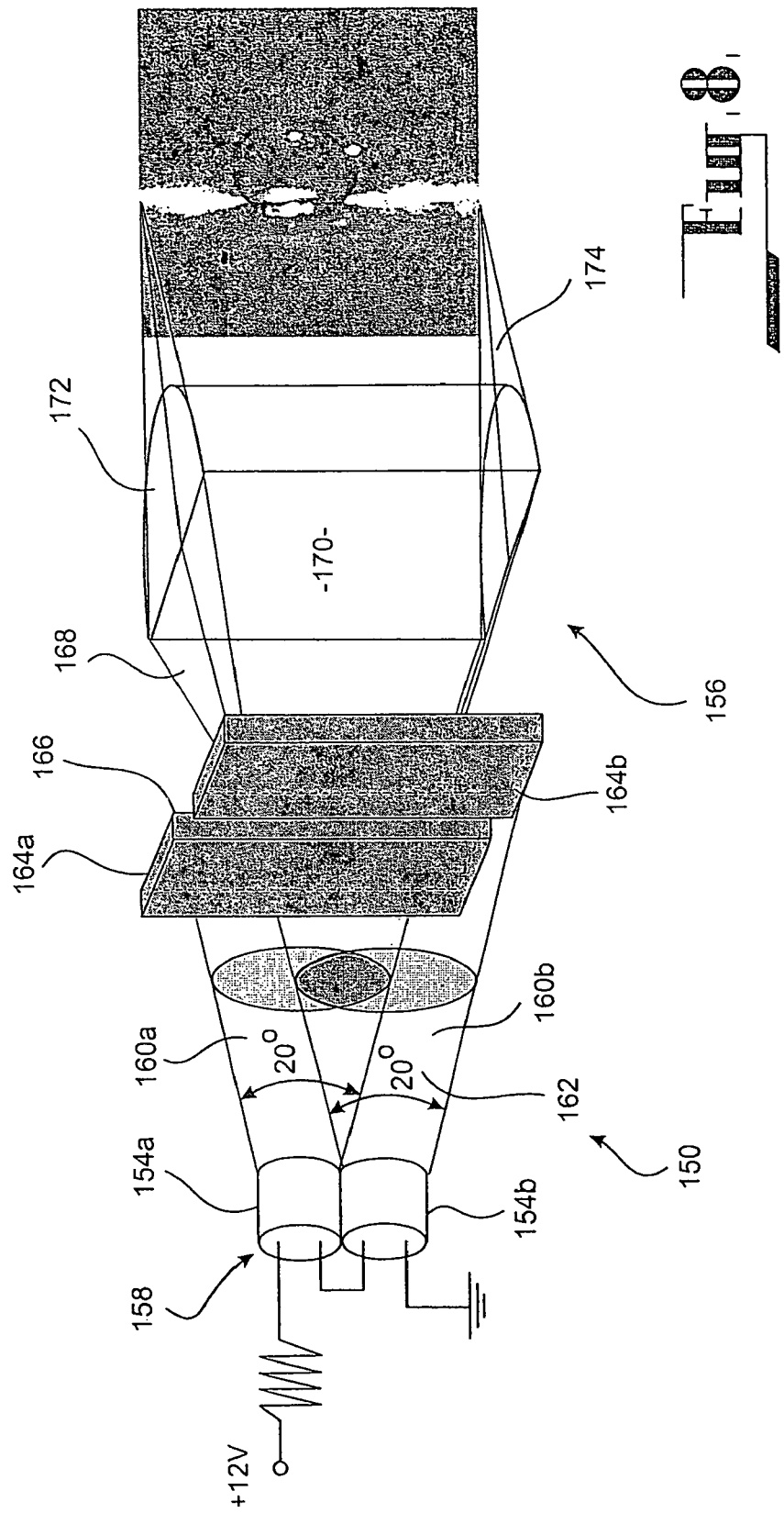

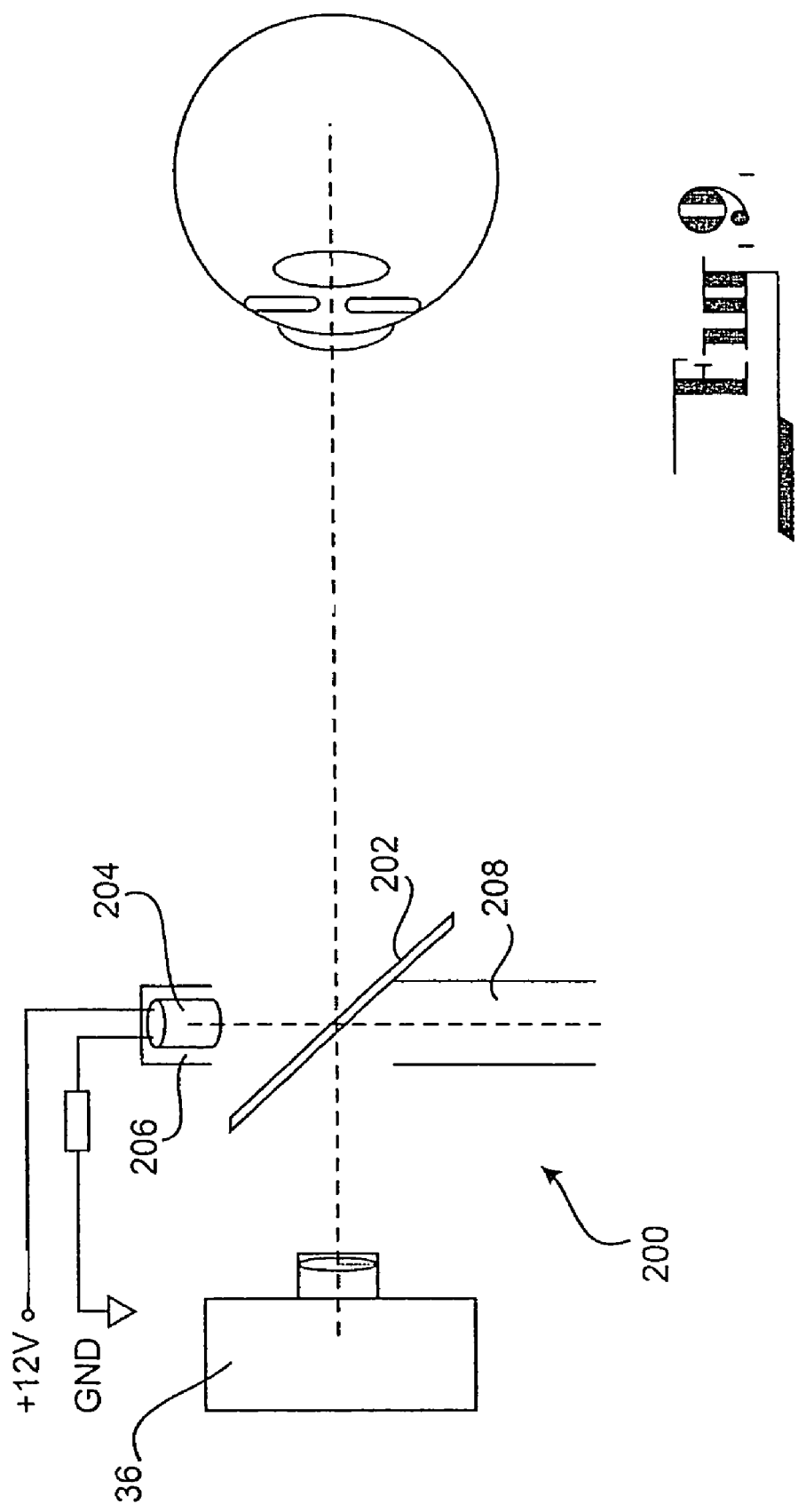

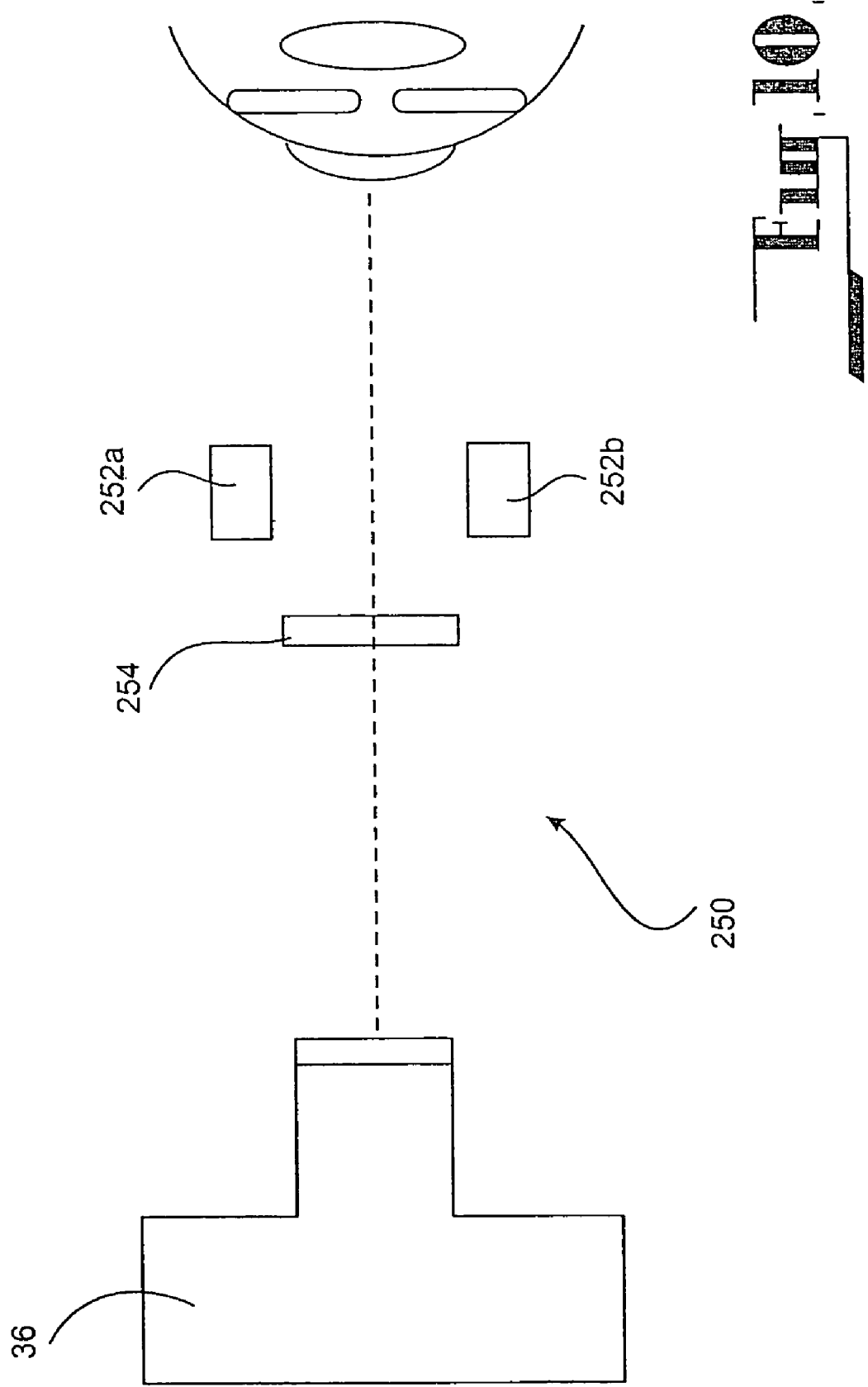

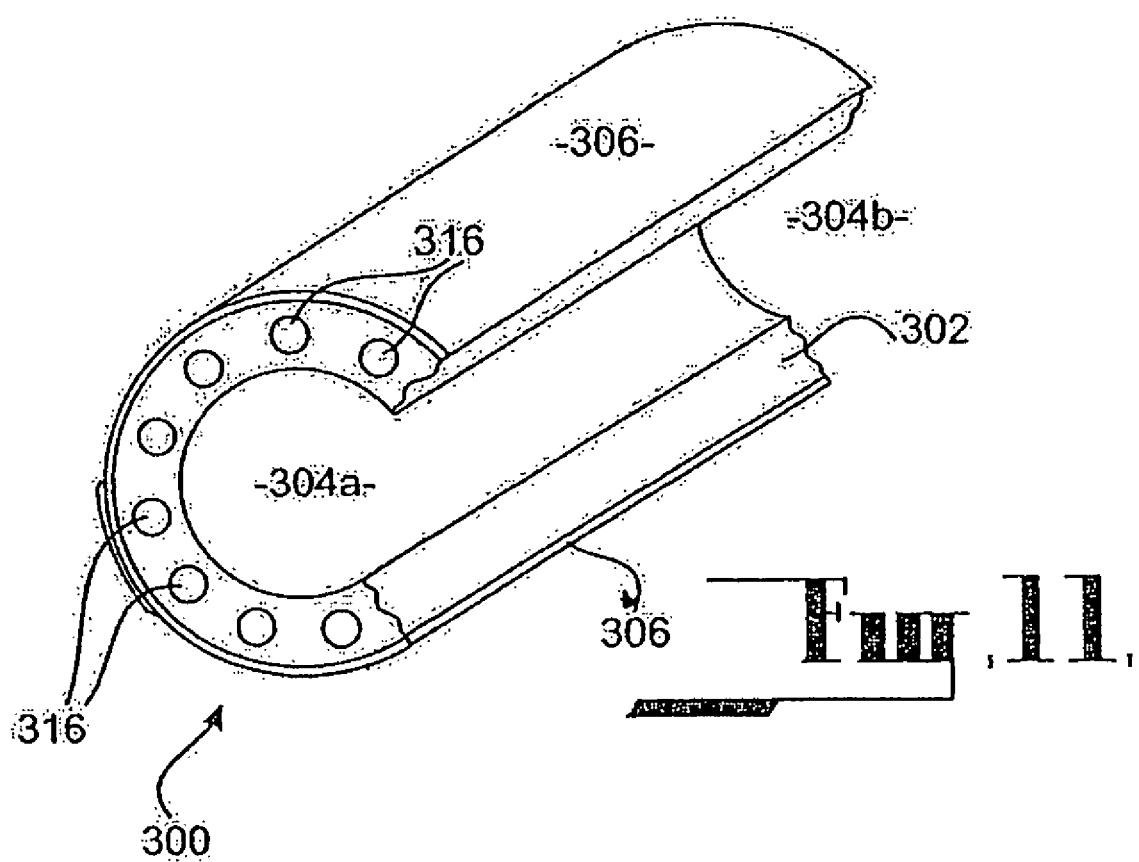

MULTI-PURPOSE IMAGING APPARATUS AND ADAPTORS THEREFOR

CROSS REFERENCE TO RELATED APPLICATIONS

This application is a continuation-in-part of International Application No. PCT/AU03/00564, filed on May 8, 2003, published as WO 03/094706 on Nov. 20, 2003, and claiming priority to Australian application PS 2190, filed on May 8, 2002.

All of the foregoing applications, as well as all documents cited in the foregoing applications ("application documents") and all documents cited or referenced in the application documents are incorporated herein by reference. Also, all documents cited in this application ("herein-cited documents") and all documents cited or referenced in herein-cited documents are incorporated herein by reference. In addition, any manufacturer's instructions or catalogues for any products cited or mentioned in each of the application documents or herein-cited documents are incorporated by reference. Documents incorporated by reference into this text or any teachings therein can be used in the practice of this invention. Documents incorporated by reference into this text are not admitted to be prior art.

FIELD OF THE INVENTION

The present invention relates to a multi-purpose imaging apparatus and adaptors therefor. The invention is particularly suitable for use in the medical fields of ophthalmology, dermatology and otolaryngology and in the field of dentistry.

Throughout the specification, unless the context requires otherwise, the word "comprise" or variations such as "comprises" or "comprising", will be understood to imply the inclusion of a stated integer or group of integers but not the exclusion of any other integer or group of integers.

BACKGROUND OF THE INVENTION

The following discussion of the background invention is intended to facilitate an understanding of the present invention. However, it should be appreciated that the discussion is not an acknowledgment or admission that any of the material referred to was published, known or part of the common general knowledge in Australia as at the priority date of the application.

Commercial medical diagnosis instruments are generally expensive to purchase. In remote or sparsely populated regions, the cost of purchasing the diagnosis instruments may be commercially unrealistic when weighed against the number of people such instruments will service. This means that the patient has to travel to a remote service provider in order to be diagnosed via such instruments. This can then be costly for the patient, both in monetary terms and possibly in health terms. Even in situations where the above problem does not exist, there may still be the problem of the lack of specialist expertise necessary to properly operate such instruments.

In PCT/AU01/00570, the applicant's describe a portable slit lamp being adapted particularly for use in sparsely populated and remote regions. However, the portable slit lamp described is limited in its diagnostic capabilities—the portable slit lamp only providing functionality for imaging the anterior segment of the eye. Further, the portable slit lamp described requires the operator to familiarise themselves with the various switches and levers provided thereon to properly operate the device.

SUMMARY OF THE INVENTION

The present invention seeks to provide a multi-purpose imaging apparatus and adaptors therefor. The optical configuration of the adaptors allow the multi-purpose imaging apparatus to perform a variety of diagnostic activities.

In this manner, the number of patients capable of being serviced by the multi-purpose imaging apparatus is increased. At the same time the versatility of the multi-purpose imaging apparatus makes it more affordable for such regions as the cost of the device can be spread against a number of health-service providers.

Ideally, the imaging means used in the multi-purpose imaging apparatus is a digital camera. Use of the digital camera is preferred as digital images are instantaneous and available in a form that allows for rapid transmission or modification as may be required. Digital images are also preferred as the can be stored on removable media.

The multi-purpose imaging apparatus also includes a simplified control structure, by which the optics of the adaptors can be controlled. This level of control extends beyond simply controlling activation of light sources contained within the adaptor and includes controlling the brightness of such light sources. The use of a simplified control structure allows people not specifically trained as medical professionals to easily operate the device in a manner that allows images taken with the apparatus to then be used by medical professionals to give an informed diagnosis.

The invention provides further advantages due to its portability. This has been achieved by both providing a case for holding the various components of the multi-purpose imaging system and by adapting the multi-purpose imaging apparatus to be held comfortably in the hand of the operator.

The adaptors designed for use with the multi-purpose imaging apparatus include connection means designed to allow for easy removal of each adaptor as required. At the same time, connection means are designed to ensure that each adaptor is securely attached to the multi-purpose imaging apparatus when in use.

Each adaptor is designed to provide a different diagnostic function. In the invention described herein, adaptors are provided to perform the following functions:
 capture slit-lamp images;
 capture red reflex images;
 image the fluorescence of the subject;
 image tear-film;
 capture images of the subject's fundus;
 take a nibut image of the subject;
 capture dental images;
 function as an otoscope; and
 capture dermatological images.

The multi-purpose imaging apparatus is also adapted for use in a system. The system, as mentioned above, includes a case for ease of portability of the apparatus and the processing unit necessary for storage and/or further processing of the images taken. Ideally, the system is connected via USB or Firewire™ connectors as these allow the multi-purpose imaging apparatus to draw power from the processing unit. However, wireless transmission can also be used, provided that the multi-purpose imaging apparatus has a separate power source.

As the combined power draw of the processing unit and multi-purpose imaging apparatus is anticipated to result in limited operational time for the apparatus, the case can be adapted to provide a backup power source or provide means for connection to an external power source, such as mains power.

The processing unit is preferably a tablet PC. The advantages of the tablet PC are discussed in more detail below.

BRIEF DESCRIPTION OF THE DRAWINGS

The invention will now be described, by way of example only, with reference to the accompanying drawings, in which:

FIG. 1 is a side view of the multi-purpose imaging apparatus with an adaptor attached thereto.

FIG. 2 is a front-side isometric view of the multi-purpose imaging apparatus of FIG. 1.

FIG. 5 is a front view of a generic adaptor and a portion of the multi-purpose imaging apparatus of FIG. 1.

FIG. 6 is a rear-side view of the generic adaptor of FIG. 5.

FIG. 7 is a sectional view of the generic adaptor of FIG. 5 attached to the portion of the multi-purpose imaging apparatus also shown in FIG. 5.

FIG. 8 is a schematic diagram of the optics and electronics of a slit lamp adaptor.

FIG. 9 is a schematic diagram of the optics and electronics of a red reflex adaptor.

FIG. 10 is a schematic diagram of the optics and electronics of a fluorescence adaptor.

FIG. 11 is a schematic diagram of the optics and electronics of a tear-film adaptor.

FIG. 15b is a side view of the optics and electronics of the otoscope adaptor shown in FIG. 15a.

DETAILED DESCRIPTION

Figure 3:
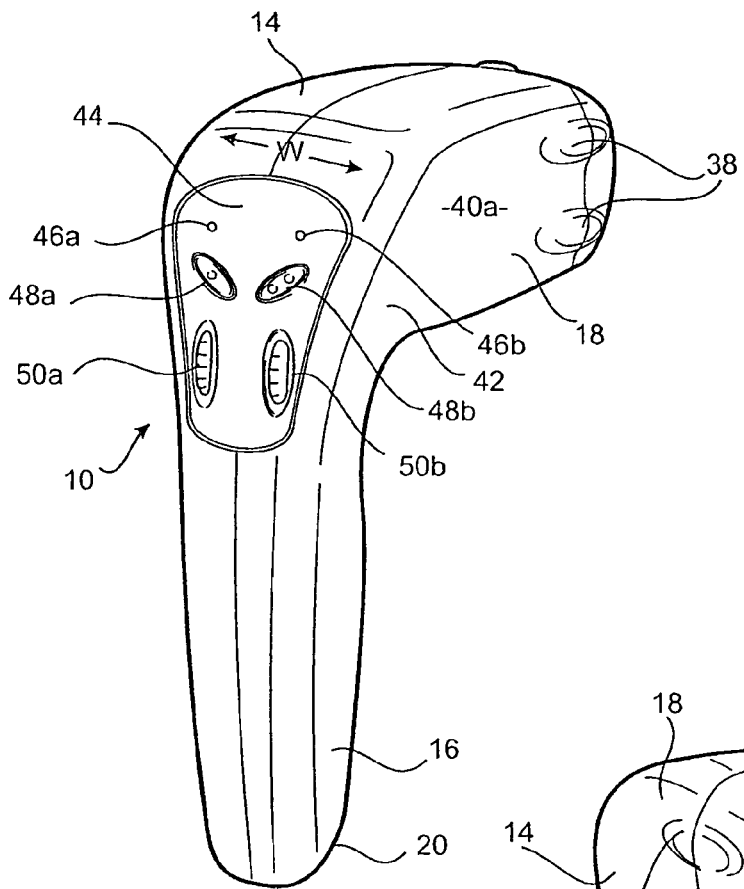
FIG. 3 is a rear-side isometric view of the multi-purpose imaging apparatus of FIG. 1.
Figure 4:
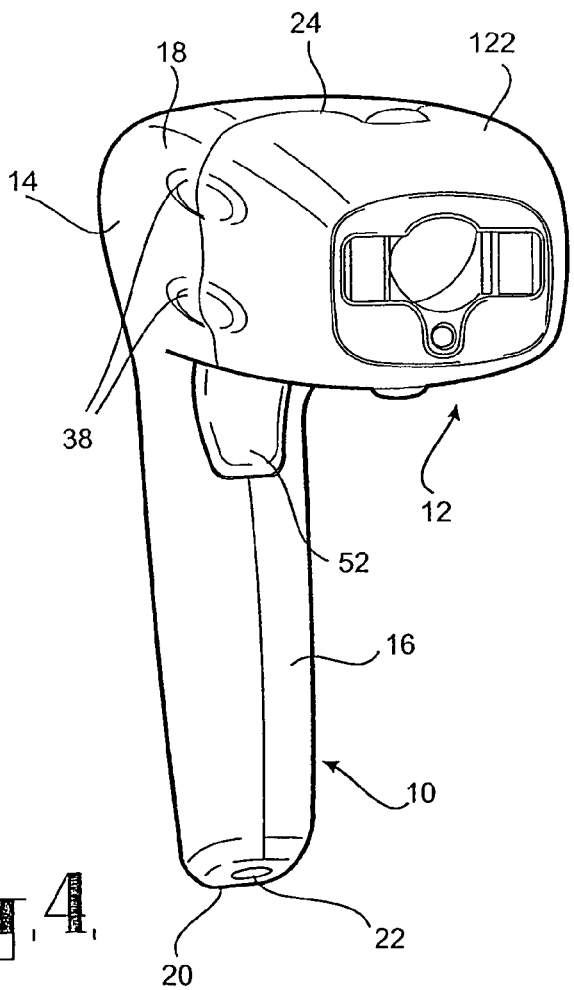
FIG. 4 is a front isometric view of the multi-purpose imaging apparatus of FIG. 1.

In accordance with a first aspect of the invention there is a multi-purpose imaging apparatus 10 having adaptors 12 therefor. The multi-purpose imaging apparatus 10 will now be described with reference to FIGS. 1 to 5.

Multi-purpose imaging apparatus 10 consists of a body 14. In the embodiment shown the body 14 is shaped like an "L". The shorter section 16 of the body 14 acts as a handle and is narrower in width W in comparison to longer section 18 of body 14. First end 20 of body 14 has an I/O port 22 located thereon. Second end 24 of body 14 is configured to receive and securely retain an adaptor 12.

Second end 24 has a recessed face 26. A lens 28 is located centrally about recessed face 26 and protrudes therefrom. Also located on recessed face 26 is an interface contact 30. In the embodiment shown, interface contact 30 is located below lens 28 when the multi-purpose imaging apparatus 10 is oriented such that an image of an object can be taken (hereafter referred to as "normal orientation"). Adjacent recessed face 26, in internal side walls 32a, 32b, are grooves 34a, 34b.

Lens 28 forms part of digital camera 36. Digital camera 36 is housed within longer section 18 of body 14. While any digital camera may be used, digital cameras having:

a frame rate of less than 15 frames per second; and/or
a resolution of greater than 30 µm spot on retinal image; and/or
a sensitivity of <1 lux,
may not be able to produce images suitable for diagnostic purposes.

Second end 24 also has a pair of grips 38 located on side 40a and side 40b. The function of grips 38 is readily apparent from the example of use of the multi-purpose imaging apparatus 10 provided below and therefore will not be discussed further here.

Located at join 42 of shorter section 16 and longer section 18 are a plurality of user controls 44. The user controls 44 are situate on the surface of join 42 that faces a user during normal orientation.

User controls 44 comprise two LEDs 46a, 46b, two push-buttons 48a, 48b and two gain-controllers 50a, 50b. User controls 44 are electronically connected to interface contact 30 and allow the user to adjust the optics and/or electrical operation of the adaptor 12 attached to the multi-purpose imaging apparatus 10. This will be described in more detail below.

Also located at join 42, but on the surface of join 42 opposite the user controls 44, is an image capture button 52. Image capture button 52 is in control communication with digital camera 36. When image capture button 52 is depressed, digital camera 36 records the image it is then focussed on and stores it in a memory (not shown).

The memory may take any form but in the embodiment described the memory may be a CompactFlash™ card, such as those available from Canon, Inc., a Sony™ memory stick available from Sony Corporation of America, or a Secure Digital Memory card, such as those available from the Hewlett-Packard Company. Irrespective of the actual form of memory chosen, memory is received and retained within I/O port 22. Memory may be removed from I/O port 22 as needed—such as in the case of memory being full of digital images or the images stored in memory being transferred to another device for further processing.

Adaptors 12 have a generic construction as shown in FIGS. 5 to 7 and this will now be described. The optics, electronics and other custom components of each adaptor 12 will be described separately.

As shown in FIG. 5, each adaptor 12 consists of a body 100. Body 100 is substantially rectangular in shape and has a rear face 102, two sides 104a, 104b and a front face 106.

Rear face 102 is of equal size and shape to recessed face 26. Located centrally about rear face 102 is an aperture 108. Aperture 108 extends through the adaptor 12 such that aperture 108 is also located centrally about front face 106. Situate adjacent aperture 108 is interface contact 110.

Adjacent rear face 102 are two snap clips 112a, 112b. Snap clip 112a extends from side 104a, while snap clip 112b extends from side 104b. Each snap clip 112 has an internal recess 114 positioned such that, when appropriate pressure is applied, the snap clips 112 can flex towards aperture 108. Snap clips 112a, 112b are adapted to be releasably retained within grooves 34a, 34b, respectively.

Surrounding front face 106, and extending along a portion of sides 104 towards rear face 102, is a rubber overmoulding 116. Rubber overmoulding 116 covers a portion 118 of each snap clip 112. Finger grips 120 are formed within the external surface 122 of rubber overmoulding 116 at a position substantially adjacent portion 118.

When snap clips 112 are releasably retained within grooves 34, the following situation exists:
- aperture 108 aligns with optical axis X of digital camera 36, such that at least a portion of the optical axis X is not obscured by the remainder of the adaptor 12;
- interface contact 110 forms a connection with interface contact 30; and
- the external surface 122 of rubber overmoulding 116 sits flush with the external surface of the multi-purpose imaging apparatus 10, thereby making it look like the adaptor 12 is integral thereto.

The optics, electronics and other custom components of each adaptor 12 will now be described.

FIG. 8 shows the optics and electronics of a slit lamp adaptor 150.

Protruding from front face 106 of slit lamp adaptor 150 are two slit-lamp devices 152a, 152b. Both slit lamp devices 152 are angled such that, when the multi-purpose hand-held imaging apparatus 10 is held at normal orientation in front of a patient's left eye, slit-lamp device 152a is operable as the slit lamp, while, when held at normal orientation in front of a patient's right eye, slit lamp device 152b is operable as the slit lamp. The operator of the multi-purpose imaging apparatus is able to select whether slit-lamp device 152a or 152b is operable in a manner described in detail below.

Each slit-lamp device 152a, 15b contains a pair of adjacent solid state lamps 154a, 154b and associated optics 156. The solid state lamps 154a, 154b are white LEDs and together combine to form light source 158. The use of LEDs is preferable to small light bulbs, due to their lower power requirements and heat dissipation as well as their internally focussed light, but is not essential to the invention.

Light source 158 generates two overlapping cones of light 160a, 160b. The overlapping cones of light 160a, 160b combined form an initial elongated beam 162. The initial elongated beam 162 is laterally trimmed by structures 164a, 164b as it passes through the narrow slit 166 formed there between.

The width of the narrow slit 166 can be adjusted by changing the position of either structure 164a, 164b or both. If the narrow slit 166 is made narrower, an optical section of the anterior part of the eye is seen. When the narrow slit 166 is made a little wider, blocks of the transparent tissues are illuminated. It is preferable that the narrow slit 166 measure about 0.08 mm.

The beam emerging from the narrow slit 166 is referred to as the intermediate beam 168. The intermediate beam 168 is then directed to the planar face 170 of a prism lens 172 of uniform semi-circular cross-section, the planar face 170 being orthogonal to intermediate beam 168. The prism lens 172 focuses the intermediate beam 168 so as to be aligned with narrow slit 166 and elongated beam 162. The prism lens 172 also longitudinally trims the intermediate beam 168 back to a segment corresponding with the segment formed by the overlapping of cones of light 160a, 160b.

The beam of light that passes through the prism lens 172 is a narrow beam of light 174. It is this narrow beam of light 174 that is focused towards the cornea of the patient's eye.

Optics 176 are fixedly received within aperture 108 to facilitate the digital camera 36 capturing an image of the reflection of narrow beam of light 174 by structures of the eye. An additional light source 178 is also located on front face 106. The additional light source 178 provides background illumination of the cornea and thus assists in providing high quality images of the eye.

FIG. 9 shows the optics and electronics of a red reflex adaptor 200.

In this adaptor, a beam splitter 202 is received within aperture 108 at a position substantially adjacent rear face 102. A light source 204, in the form of a white LED, is positioned above the beam splitter 202 in a recess 206. The alignment of the light source 204 relative to optical axis X is such that the angle there between, as measured at the position of beam splitter 202, is 90°.

In this configuration, light emitted from light source 204 is directed towards beam splitter 202 (recess 206 absorbing any dispersed light). Upon contact with beam splitter 202, the light is split such that some light is reflected 90° along optical axis X directly towards the patient's eye.

As the light that passes through beam splitter 202 can cause unwanted reflections that interfere with the integrity of the images to be recorded, an additional aperture 208 is formed within red reflex adaptor 200. Additional aperture 208 extends through body 100 at a position transverse to aperture 108. Additional aperture 208 is in the same plane as, and of substantially the same size and shape as, light source 204. In this manner, light that passes through beam splitter 202 is directed along additional aperture 208 until it exits the body 100 of red reflex adaptor 200.

FIG. 10 shows the optics and electronics of a fluorescence adaptor 250.

The optics and electronics of fluorescence adaptor 250 comprises two blue diodes 252a, 252b and a yellow filter 254. Blue diodes 252a, 252b protrude from the front face 106 of fluorescence adaptor 250. Yellow filter 254 is received within aperture 108 in the path of optical axis X.

The two blue diodes 252a, 252b are used to evenly illuminate the eye to be imaged. Yellow filter 254 operates to cut out any reflected light directed towards digital camera 36.

FIG. 11 shows the optics and electronics of a tear-film adaptor 300.

Fixedly received within aperture 108 is a hollow, transparent cylinder 302 having open ends 304a, 304b. The cylinder 302 is of equal dimension to that of aperture 108, such that end 304a sits flush with front face 106 and end 304b sits flush with rear face 102.

A sheet of reflective film 306 surrounds the external wall 308 of cylinder 302. The combination of reflective film 306 and cylinder 302 produces a mirror effect.

Located at open end 304a of cylinder 302 is a plurality of LEDs 316. LEDs 316 are equidistantly spaced around the circumference of end 304a. The number, and therefore the spacing, of the LEDs 316 must be such as to produce a homogenous light source.

Figure 12:
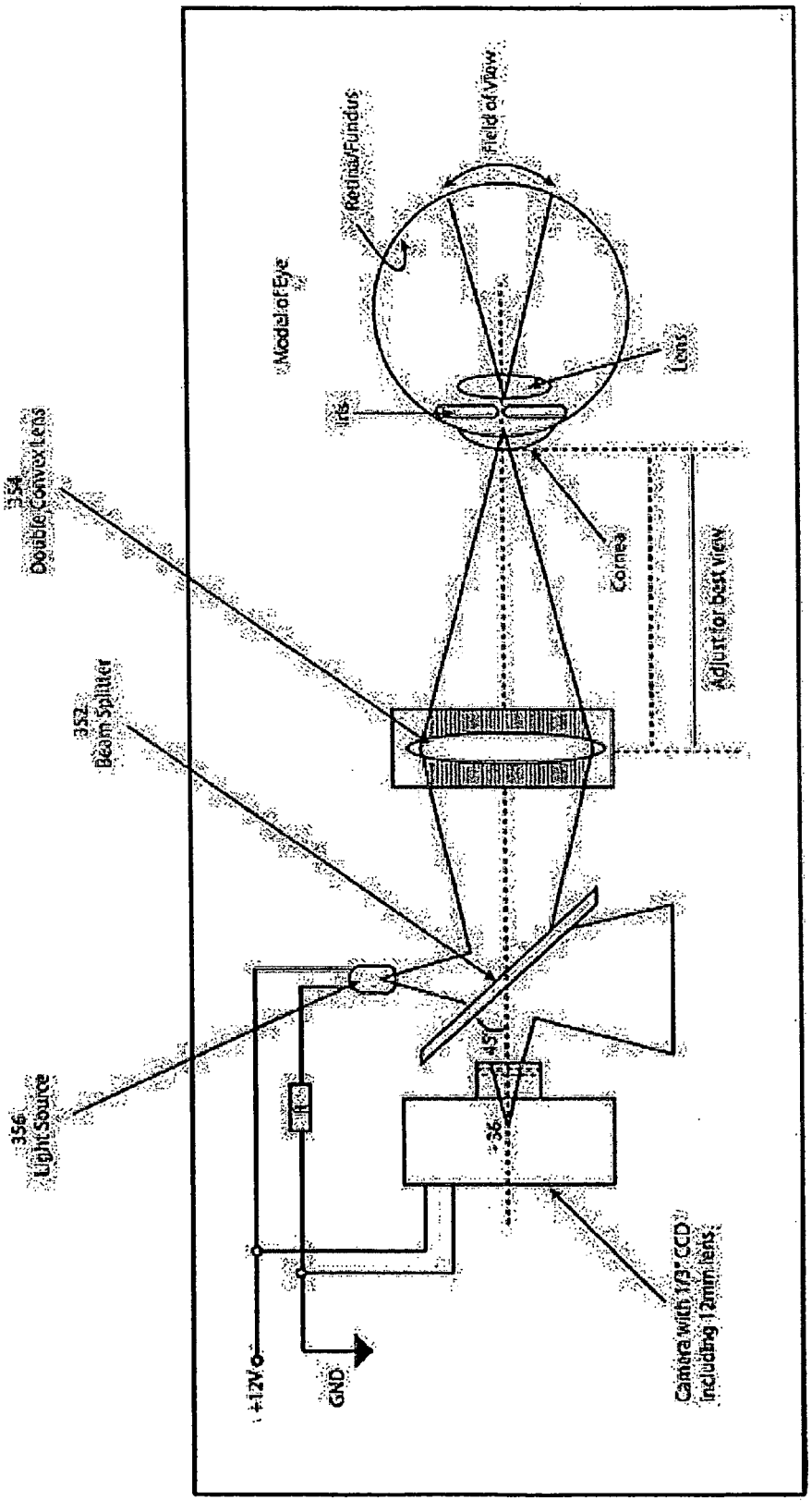
FIG. 12 is a schematic diagram of the optics and electronics of a fundus adaptor.

FIG. 12 shows the optics and electronics of a fundus adaptor 350.

In this adaptor, a beam splitter 352 and double convex lens 354 is received within aperture 108. Beam splitter 352 is substantially adjacent rear face 102. Double convex lens 354 is substantially adjacent front face 106.

A light source 356, in the form of a white LED, is positioned above the beam splitter 352 in a recess 358. The alignment of the light source 356 relative to double convex lens 354 is such that the angle there between, as measure at the position of beam splitter 352, is 90°.

In this configuration, light emitted from light source 356 is directed towards beam splitter 352 (recess 358 absorbing any dispersed light). Upon contact with beam splitter 352, the light is split such that some light is reflected 90° towards the double convex lens 354. This light is then focused by the double convex lens 354 such that the light can penetrate the iris and lens to display the fundus of a patient's eye. The remaining light passes through beam splitter 352.

As the light that passes through beam splitter 352 can cause unwanted reflections that interfere with the integrity of the image of the fundus to be recorded, an additional aperture 360 is formed within fundus adaptor 350. Additional aperture 360 extends through body 100 at a position transverse to aperture 108. Additional aperture 360 is in the same plane as, and of substantially the same size and shape as, light source 356. In this manner, light that passes through beam splitter 352 is directed along additional aperture 360 until it exits the body 100 of fundus adaptor 350.

Figure 13:
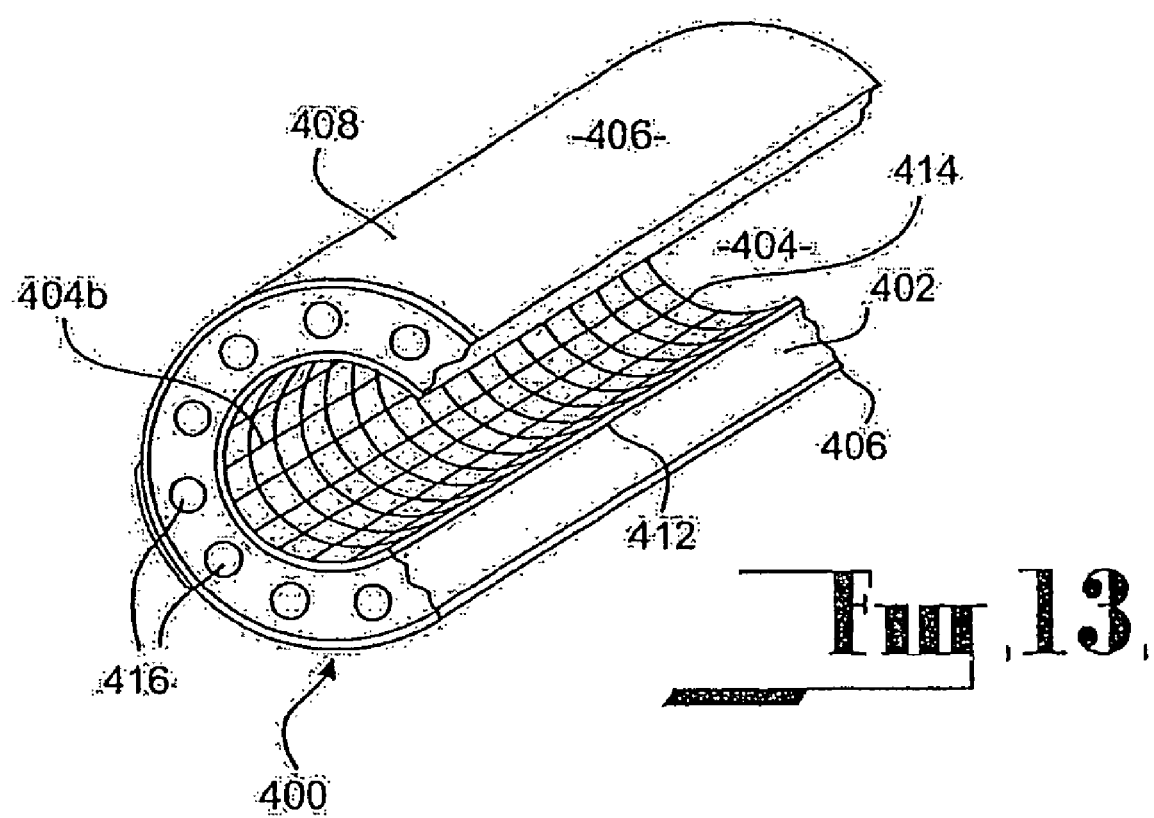
FIG. 13 is a schematic diagram of the optics and electronics of a nibut adaptor.

FIG. 13 shows the optics and electronics of a nibut adaptor 400.

Fixedly received within aperture 108 is a hollow, transparent cylinder 402 having open ends 404a, 404b. The cylinder 402 is of equal dimension to that of aperture 108, such that end 404a sits flush with front face 106 and end 404b sits flush with rear face 102.

A sheet of reflective film 406 surrounds the external wall 408 of cylinder 402. The combination of reflective film 406 and cylinder 402 produces a mirror effect.

A transparent sheet 410 surrounds the internal wall 412 of cylinder 402. Transparent sheet 410 has a grid pattern 414 printed thereon.

Located at open end 404b of cylinder 402 is a plurality of LEDs 416. LEDs 416 are equidistantly spaced around the circumference of end 404b. The number, and therefore the spacing, of the LEDs 416 must be such as to produce a homogenous light source.

Figure 14:
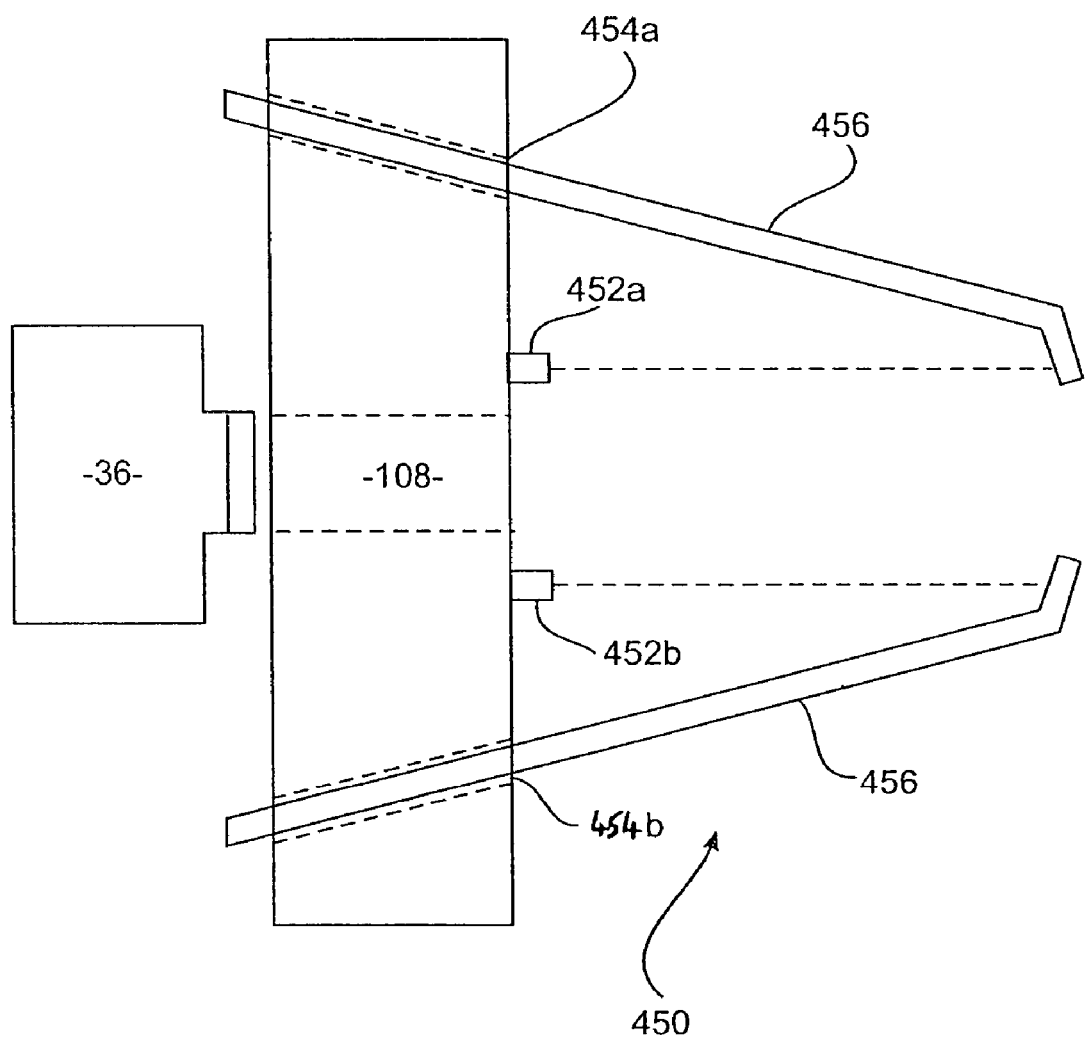
FIG. 14 is a top plan view of a dental adaptor.

FIG. 14 shows a top plan view of a dental adaptor 450.

Dental adaptor 450 comprises two light sources 452a, 452b and two angled apertures 454a, 454b. Light sources 452a, and 452b protrude from front face 106 at opposite positions respective to aperture 108. Angled apertures 454a, 454b extend through the body 100 of dental adaptor 450, again at opposite positions respective to aperture 108 and in alignment with the positions of light sources 452a, 452b. Thus, angled aperture 454a corresponds with light source 452a and angled aperture 454b corresponds with light source 452b.

Angled apertures 454a, 454b are each adapted to receive a dental mirror 456. The size of the apertures 454a, 454b is such that dental mirrors 456 are firmly retained therein, but not to the extent that dental mirrors 456 can not have its position therein slidably adjusted.

In the embodiment shown, the angle of angled apertures 454a, 454b relative to front face 106 is 83°. However, the angle of angled apertures 454a, 454b is determined by the distance between such apertures 454 and their respective light source 452. To elaborate, the angle should be such that light source 452 directs light towards the mirror portion 458 of a dental mirror 456 retained within its corresponding angled aperture 454.

Figure 15A:
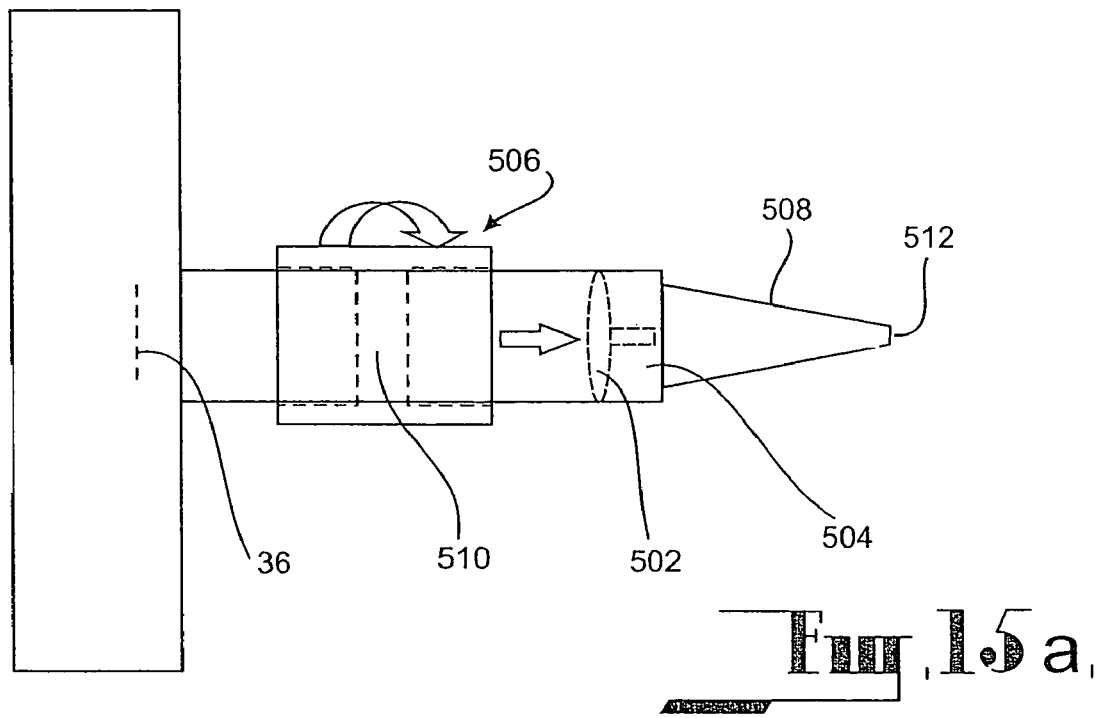
FIG. 15a is a top-view schematic diagram of the optics and electronics of an otoscope adaptor.
Figure 15B:
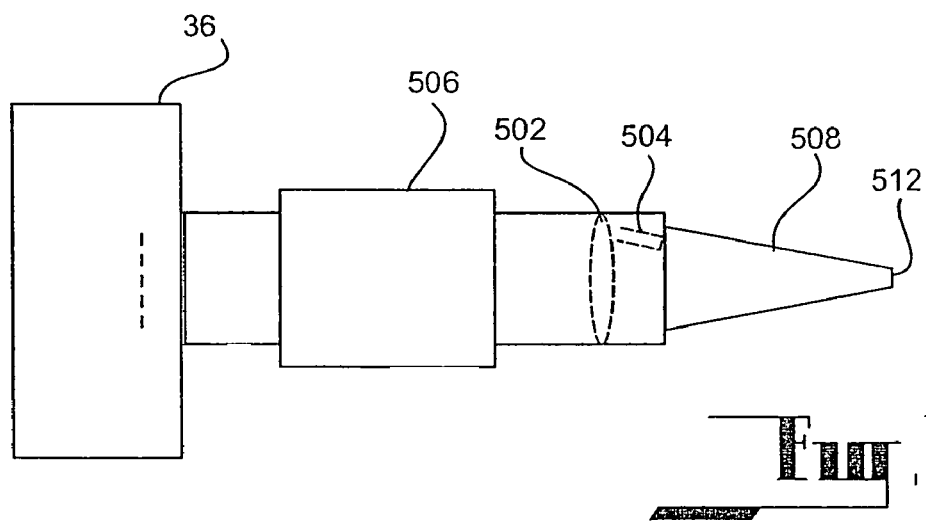

FIGS. 15a and 15b show the optics and electronics of an otoscope adaptor 500.

Otoscope adaptor 500 comprises lens 502, light source 504, focusing means 506 and ear plug 508.

Lens 502 is fixedly received within aperture 108 at a position substantially adjacent to, but spaced form front face 106. Light source 504, in the form of an LED, is located within the area of aperture 108 between lens 502 and front face 106. The orientation of light source 504 is described below.

In the embodiment shown focusing means 506 takes the form of a lens slider 510. Rotation of lens slider 510 adjusts the distance between video camera 36 and lens 502, thereby adjusting the focus of lens 502.

Ear plug 508 is adapted to be received on front face 106 of the otoscope adaptor. Ear plug 508 is identical to ear plugs used in standard hand-held otoscopes, having a small opening at end 512.

Light source 504 is disposed towards the perimeter of aperture 108 and oriented such that light therefrom is directed out through the small opening at end 512.

Figure 16:
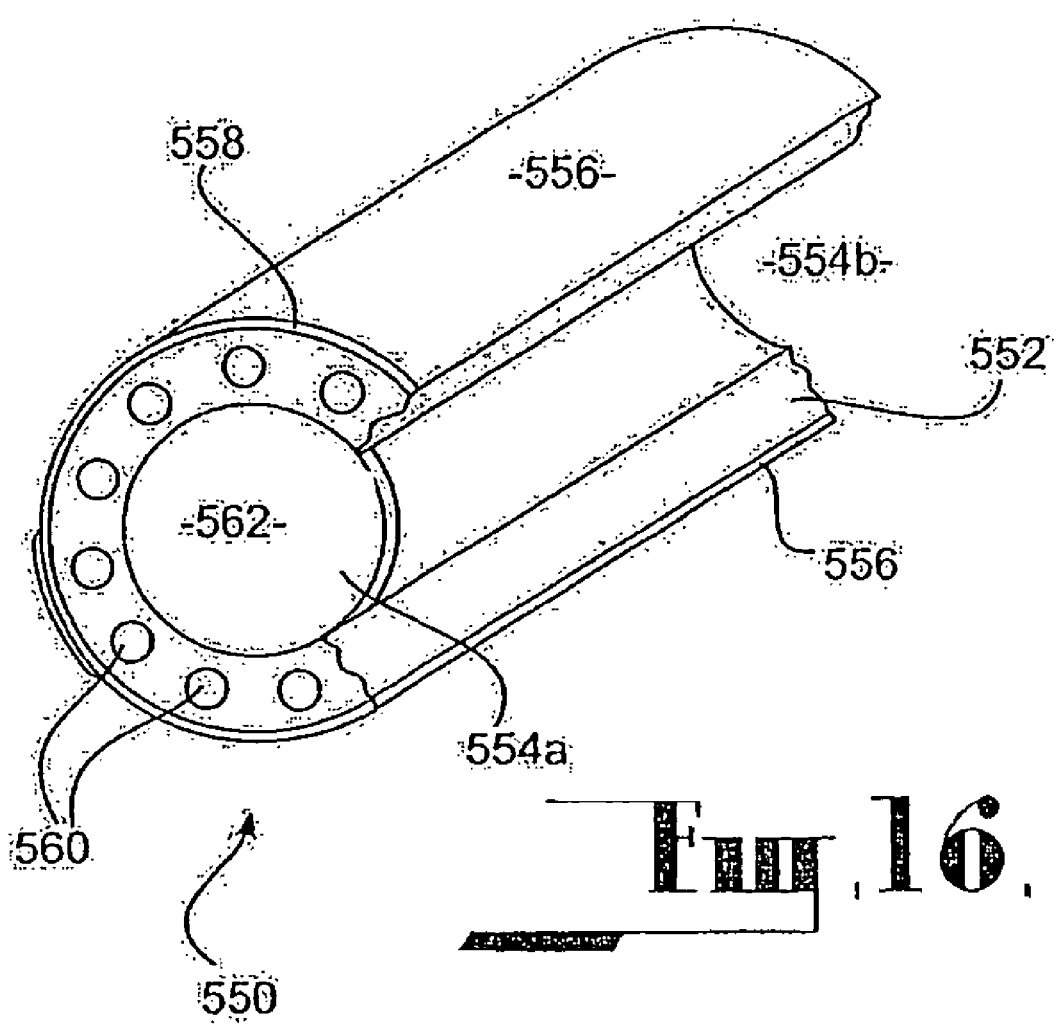
FIG. 16 is a schematic diagram of the optics and electronics of a dermatological adaptor.

FIG. 16 shows the optics and electronics of a dermatological adaptor 550.

Fixedly received within aperture 108 is a hollow, transparent cylinder 552 having open ends 554a, 554b. The cylinder 552 is of equal dimension to that of aperture 108, such that end 554a sits flush with front face 106 and end 554b sits flush with rear face 102.

A sheet of reflective film 556 surrounds the external wall 558 of cylinder 552. The combination of reflective film 556 and cylinder 552 produces a mirror effect.

Located at open end 554a of cylinder 552 is a plurality of LEDs 560. LEDs 560 are equidistantly spaced around the circumference of end 554a. The number, and therefore the spacing, of the LEDs 560 must be such as to produce a homogenous light source.

Also positioned at open end 554a of cylinder 552 is a magnifying lens 562. In the embodiment shown, magnifying lens 562 magnifies the area to be imaged by a factor of 10. However, magnifying lenses 562 of various magnification ratings can be used.

In accordance with a second aspect of the invention, where like numerals reference like parts, there is a multi-purpose imaging system 600. The multi-purpose imaging system 600 comprises the multi-purpose imaging apparatus 10 and each adaptor 12 as described in the first aspect of the invention and a processing unit 602. Each of the aforementioned components 10, 12, 602 are received within pre-moulded compartments 604 of case 606. This allows the components of the multi-purpose imaging system 600 to be ported from one location to another in a tidy and efficient manner.

Figure 17:
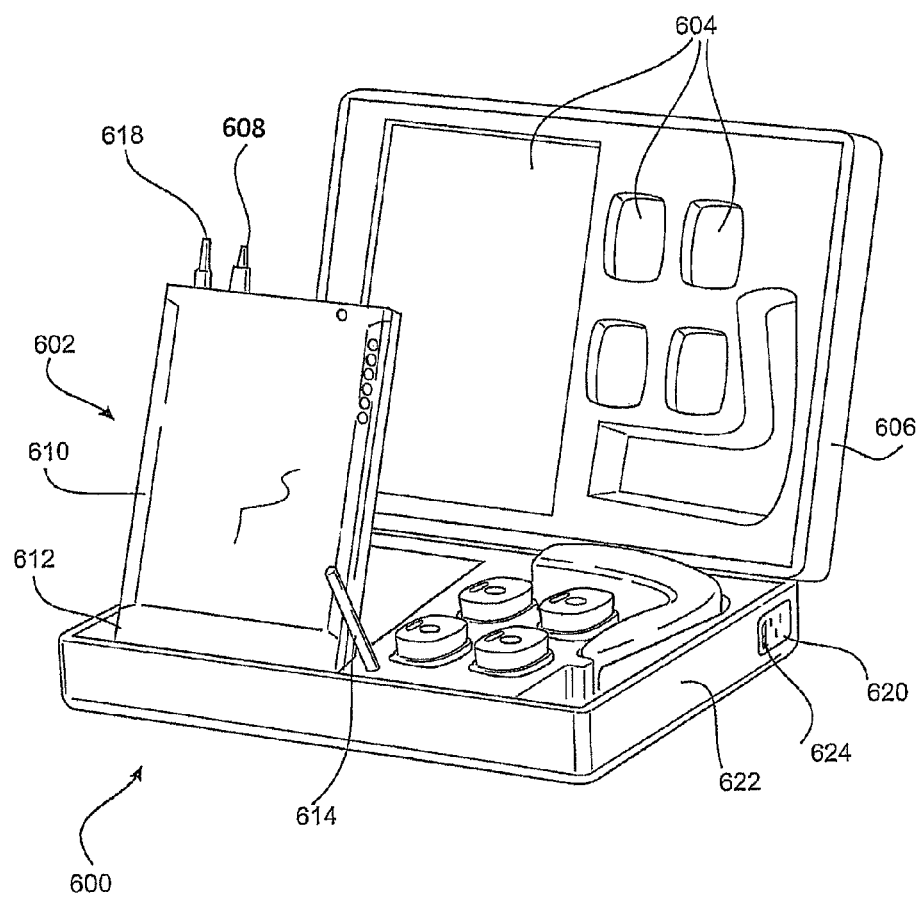
FIG. 17 is a front-side isometric view of the components that form a multi-purpose imaging system.

In the embodiment of the second aspect of the invention shown at FIG. 17, the multi-purpose imaging apparatus 10 has been modified from that described above. In place of memory received within I/O port 22, I/O port 22 is adapted to receive one end of a USB cable 608. The other end of the USB cable 608 is connected to processing unit 602.

The modification of the multi-purpose imaging apparatus 10 to receive USB cable 608 has significant, but not essential, design advantages. In particular, a USB connection allows data to be transferred from the multi-purpose imaging apparatus 10 to processing unit 602 at a high transfer rate. Furthermore, it allow the multi-purpose imaging apparatus 10 to draw power from the processing unit 602—thereby negating the need for a separate power supply.

In the embodiment shown, processing unit 602 takes the form of a tablet PC 610. Tablet PC 610 is adapted to be raised from its pre-moulded compartment 604 by pivoting about pivot point 612.

The choice of a tablet PC 610, in preference to a notebook or desktop computer, provides further design advantages to the system. In particular, a tablet PC 610 is robust and easy to use, with data being able to be entered through a stylus 614 rather than a keyboard. At the same time, a tablet PC is primed for voice command. The hardware configuration of current tablet PCs is also sufficient for intended purposes. The low weight aspect of tablet PCs and large high-resolution screen sizes are also distinct advantages.

Case 606 has a built-in power transformer 616. The power transformer (not shown) provides power to the tablet PC 610 via cable 618. For ease of use, the power transformer (not shown) has a power connector 620 built into a sidewall 622 of the case 606. The power connector 620 in the embodiment shown is adapted to receive a standard 3-pin power cable (not shown). The power connector 620 also includes a power switch 624 for turning the power transformer 616 on or off.

In addition to providing power to the tablet PC 610, the power transformer (not shown) is attached to a battery (not shown) built into case 606. This battery provides additional power to the tablet PC 610 as needed.

Use of the multi-purpose imaging apparatus 10 will now be described in the context of the multi-purpose imaging system 600 described above.

Case 606 is opened to reveal the multi-purpose imaging apparatus 10, adaptors 12 and tablet PC 610. Tablet PC 610 is then pivoted about pivot point 612 until it reaches a position the operator finds comfortable for use. Multi-purpose imaging apparatus 10 is thereafter connected to tablet PC 610 via USB cable 608.

As mentioned above, the use of USB cable 608 provides power to the multi-purpose imaging apparatus 10. If the tablet PC 610 has a single full battery and is not drawing power from an external power source, the multi-purpose imaging system 600 is expected to be operable for a period of between 1 and 2 hours. For the multi-purpose imaging system 600 to be operable for a longer period of time, it is recommended that a connection to mains power or some other form of power supply be made or the battery that forms part of case 606 be utilised. In respect of the former recommendation, this can be achieved by inserting one end of a standard 3-pin power cable (not shown) into power connector 620 and inserting the other end into mains power or the alternate power supply. If not already connected, cable 618 must then be received within the power connector of tablet PC 610 and power switch 624 set to on.

A discussion will now be made of each of the adaptors 12 in the order they have been described above. However, it should be appreciated by the person skilled in the art that this is done for illustrative purposes only.

Slit lamp adaptor 150 is attached to multi-purpose imaging apparatus 10 by applying force to the adaptor 12 until snap clips 112 engage grooves 34. This method is illustrated in FIGS. 5 and 6.

Multi-purpose imaging apparatus 10 is then raised to a level and position where slit lamp devices 152 are held directly in front of a patient's eye. To facilitate the comfort of the operator the operator may grip the multi-purpose digital imaging apparatus 10 about grips 38.

If the slit lamp device 152 is held directly in front of the patient's right eye, the operator depresses push-button 48a. In the context of this adaptor 12, depressing push-button 48a activates slit lamp device 152b and additional light source 178. This also causes LED 46a to light and thereby inform the operator that the multi-purpose imaging apparatus 10 is set to image the patient's right eye.

Activation of slit lamp device 152b results in narrow beam of light 174 extending therefrom in accordance with the description of the optical arrangement given above. Operation of the multi-purpose imaging apparatus 10 then proceeds in the same manner as it would if a normal slit lamp were being operated.

Depression of image capture button 52 causes digital camera 36 to capture an image of the reflection of narrow beam of light 174 by structures of the eye, the image being substantially the exact slit image seen directly from the multi-purpose imaging apparatus 10. The image is then downloaded, via USB cable 608 to tablet PC 610 for storage and/or further processing.

If the operator needs to vary the brightness of light produced by light source 158, for example, in situations where the patient's iris is blue or brown or of an otherwise darker colouring, this can be achieved by appropriate manipulation of gain controller 50a. If the operator needs to vary the brightness of light produced by additional light source 178, and thereby adjust the level of background illumination, this can be achieved by appropriate manipulation of gain controller 50b.

If the slit lamp device 152 is held directly in front of the patient's left eye, the operator depresses push-button 48b. In the context of this adaptor 12, depressing push-button 48b activates slit lamp device 152a and additional light source 178. This also causes LED 46b to light and thereby inform the operator that the multi-purpose imaging apparatus 10 is set to image the patient's left eye.

Activation of slit lamp device 152a results in narrow beam of light 174 extending therefrom in accordance with the description of the optical arrangement given above. Operation of the multi-purpose imaging apparatus 10 then proceeds in the same manner as it would if a normal slit lamp were being operated.

Depression of image capture button 52 causes digital camera 36 to capture an image of the reflection of narrow beam of light 174 by structures of the eye, the image being substantially the exact slit image seen directly from the multi-purpose imaging apparatus 10. The image is then downloaded, via USB cable 608 to tablet PC 610 for storage and/or further processing.

If the operator needs to vary the brightness of light produced by light source 158, for example, in situations where the patient's iris is blue or brown or of an otherwise darker colouring, this can be achieved by appropriate manipulation of gain controller 50b. If the operator needs to vary the brightness of light produced by additional light source 178, and thereby adjust the level of background illumination, this can be achieved by appropriate manipulation of gain controller 50a.

It is to be noted that only one slit lamp device 152 can be operated at any one time. Accordingly, if slit-lamp device 152b is activated, depression of push-button 48a operates to deactivate slit-lamp device 152b. Similarly, if slit-lamp device 152b is activated, depression of push-button 48b operates to deactivate slit-lamp device 152a. Only one of LEDs 46a, 46b is then lit as is appropriate for the new mode of operation of the multi-purpose imaging apparatus 10.

Removal of slit-lamp adaptor 150 is then achieved by applying pressure to finger grips 120 such that snap clips 112 move within their respective internal recesses 114 towards aperture 108. This movement causes snap clips 112 to dislodge from grooves 34. Slit lamp adaptor 150 can then be easily removed.

With slit lamp adaptor 150 removed, red reflex adaptor 200 can be attached to the multi-purpose imaging apparatus 10. Attachment of red reflex adaptor 200 follows the same procedure as described above for attaching slit-lamp adaptor 150.

Once attached, multi-purpose imaging apparatus 10 is then raised to a level and position where light travelling along the optical axis X of digital camera 36 is directed towards the patient's eye.

Depression of push button 48b toggles activation of light source 204. When light source 204 is activated, LED 46b is lit. As with the slit-lamp adaptor 150, the brightness of light source 204 can be controlled by appropriate manipulation of gain controller 50b.

Operation of the multi-purpose imaging apparatus 10 then proceeds in the same manner as it would if a normal red reflex generation device were being operated. Depression of the image capture button 52 causes digital camera 36 to capture the red reflex image. The image is then downloaded, via USB cable 608 to tablet PC 610 for storage and/or further processing.

So as to obtain red reflex images from the back of the eye, it is recommended that light travelling along optical axis X be directed towards the patient's eye off the central optical axis. Ideally, the angle for direction of such light is between 5° and 20°.

Once all required red reflex images have been captured, the red-reflex adaptor 200 is replaced with the fluorescence adaptor 250. The procedure of removing an adaptor 12 and attaching another adaptor 12 has been described above and will not be repeated again.

Before using the multi-purpose imaging apparatus 10 in this configuration, a fluorescent dye is projected into the patient's eyes.

The multi-purpose imaging apparatus 10 is then raised to a level and position such that, when activated, blue diodes 252 illuminate the fluorescent dye projected into the patient's eye to be imaged.

Depression of push-button 48b toggles activation of blue diodes 252. If blue diodes 252 are activated, LED 46b is lit. As with the slit-lamp adaptor 150, the brightness of blue diodes 252 can be controlled by appropriate manipulation of gain controller 50b.

Operation of the multi-purpose imaging apparatus 10 then proceeds in the same manner as it would if a normal fluorescent imaging device were being operated. Depression of the image capture button 52 causes digital camera 36 to capture an image of the fluorescence of the dye. The location of yellow filter 254 causes the image to have a slight yellow tinge to the image, however, as mentioned above, this assists in cutting out any reflected light. The image is then downloaded, via USB cable 608 to tablet PC 610 for storage and/or further processing.

Once all required fluorescent images have been captured, the fluorescence adaptor 250 is replaced with the tear-film adaptor 300.

Multi-purpose imaging apparatus 10, having tear-film adaptor 300 attached thereto, is raised to a level and position where light travelling along the optical axis X of digital camera 36 is directed towards the patient's eye.

Depression of push button 48b toggles activation of LEDs 316. When LEDs 316 are activated, LED 46b is lit. As with the slit-lamp adaptor 150, the brightness of LEDs 316 can be controlled by appropriate manipulation of gain controller 50b.

Operation of the multi-purpose imaging apparatus 10 then proceeds in the same manner as it would if a normal tear-film analyser were being operated. Depression of the image capture button 52 causes digital camera 36 to capture an image of tear-film. The image is then downloaded, via USB cable 608 to tablet PC 610 for storage and/or further processing.

Once all required tear-film images have been captured, the tear-film adaptor 300 is replaced with fundus adaptor 350.

Multi-purpose imaging apparatus 10 is then raised to a level and position where light travelling along the optical axis X of digital camera 36 is directed towards the patient's eye.

Depression of push button 48b toggles activation of light source 356. When light source 356 is activated, LED 46b is lit. As with the slit-lamp adaptor 150, the brightness of light source 356 can be controlled by appropriate manipulation of gain controller 50b.

Operation of the multi-purpose imaging apparatus 10 then proceeds in the same manner as it would if a normal fundus camera were being operated. Depression of the image capture button 52 causes digital camera 36 to capture an image of the fundus. The image is then downloaded, via USB cable 608 to tablet PC 610 for storage and/or further processing.

Once all required images of the fundus of the eye have been captured, the fundus adaptor 350 is replaced with nibut adaptor 400.

Multi-purpose imaging apparatus 10 is raised to a level and position where light travelling along the optical axis X of digital camera 36 is directed towards the patient's eye.

Depression of push button 48b toggles activation of LEDs 416. When LEDs 416 are activated, LED 46b is lit. As with the slit-lamp adaptor 150, the brightness of LEDs 416 can be controlled by appropriate manipulation of gain controller 50b.

Activation of LEDs 416 causes a series a circular grid arrangement to be formed on the eye. This grid can then be used as a reference for the location of abnormalities of the eye or other points of interest.

Depression of the image capture button 52 causes digital camera 36 to capture an image of the eye complete with circular grid arrangement. The image is then downloaded, via USB cable 608 to tablet PC 610 for storage and/or further processing.

Once all images requiring the nibut adaptor 400 have been captured, the nibut adaptor 400 is replaced with dental adaptor 450.

After attaching the dental adaptor 450, a sterilised dental mirror 456 is inserted either in angled aperture 454a or 454b as best suits the operator and activity to be performed.

Depression of push button 48b toggles activation of light source 452 corresponding with the angled aperture 454 having dental mirror 456 received therein. When light source 452 is activated, LED 46b is lit. As with the slit-lamp adaptor 150, the brightness of light source 452 can be controlled by appropriate manipulation of gain controller 50b.

When light source 452 is activated, light source 452 directs light onto the mirror portion of dental mirror 456 where it is reflected. The operator can then use this reflected light to view areas of the mouth not otherwise readily visible. While not apparent from FIG. 14, the mirror portion of dental mirror 456 is within optical axis X of digital camera 36, allowing the operator to captured an image of any area of the mouth viewed using dental mirror 456 upon depression of image capture button 52. Captured images are then downloaded, via USB cable 608 to tablet PC 610 for storage and/or further processing.

Once all dental images have been captured, the dental adaptor 450 is replaced with otoloscope adaptor 500. The dental mirror 456 is also removed from the dental adaptor and sterilised for later use.

After attaching the otoloscope adaptor 500, an ear plug 508 is attached to front face 106 thereof. The otoloscope adaptor 500 is then positioned such that ear plug 508 is inserted into the patient's ear.

Depression of push button 48b toggles activation of LED 504. When LED 504 is activated, LED 46b is lit. As with the slit-lamp adaptor 150, the brightness of LED 504 can be controlled by appropriate manipulation of gain controller 50b.

When LED 504 is activated, LED 504 directs light through the small opening at end 512 and into the patient's ear. As the depth of insertion of the ear plug 508 into the ear of a patient varies from patient to patient, the operator can focus the images provided to digital camera 36 by manipulating lens slider 510 in an appropriate manner.

By depressing image capture button 52, an image of the patient's ear is captured by digital camera 36. Captured images are then downloaded, via USB cable 608 to tablet PC 610 for storage and/or further processing.

Once all required images of the patient's ear have been captured, the otoscope adaptor 500 is replaced with dermatological adaptor 550. Ear plug 508 is removed from the otoscope adaptor 500 and disposed of.

Multi-purpose imaging apparatus 10 is then positioned such that front face 106 of dermatological adaptor 550 abuts the area of the patient's skin sought to be imaged.

Depression of push button 48b toggles activation of LEDs 560. When LEDs 560 are activated, LED 46b is lit. As with the slit-lamp adaptor 150, the brightness of LEDs 560 can be controlled by appropriate manipulation of gain controller 50b.

The operator is thereafter free to move the multi-purpose imaging apparatus 10 along the patient's skin. Depression of the image capture button 52 causes digital camera 36 to capture an image of the skin at a magnification of ×10 due to magnifying lens 562. The image is then downloaded, via USB cable 608 to tablet PC 610 for storage and/or further processing.

Once all dermatological images have been captured, the front face of dermatological adaptor 550 is wiped to remove any contaminants, before being removed from the multi-purpose imaging apparatus 10. Multi-purpose imaging apparatus 10 and adaptors 12 are then replaced into their respective pre-moulded compartments 604.

It should be noted from the above description that user controls 44 have been described as would be convenient for a right-handed operator. However, user controls 44 could be reversed to accommodate a left-handed operator, for instance, through a change in software uploaded from tablet PC 610. Furthermore, with the exception of the multi-purpose imaging apparatus 10 having slit-lamp adaptor 150 attached thereto, the choice of set of controls used could be indicative to the tablet PC 610 of the eye being imaged. To elaborate, use of push-button 48a and gain controller 50a would be indicative to the tablet PC 610 that the patient's right eye was being imaged, while use of push-button 48b and gain controller 50b would be indicative to the tablet PC 610 that the patient's left eye was being imaged.

In alternative arrangements of the slit-lamp adaptor 150, slit-lamp devices 152 may be mounted in a manner that allows for horizontal and/or vertical angular adjustment relative to normal orientation of the multi-purpose imaging apparatus 10.

In alternative arrangements of the fluorescence adaptor 250, blue diodes 252a, 252b may be replaced with an alternative light source and blue filter arrangement. Furthermore, the fluorescence adaptor 250 may be configured with more or less blue diodes 252.

In alternative arrangements of the second embodiment, in addition to user controls 44, vocal commands may be given by the operator to the tablet PC 610, the tablet PC 610 operable to execute such commands (for example, capture an image, etc.). Case 606 may also have incorporated therein headset apparatus to allow for correct positioning of a patient's head during operation. Further, an IrDA keyboard may be built into the lid of case 606.

In yet still further alternative arrangements of the second embodiment, the USB connection may be replaced with a Firewire™ connector. Alternatively, all forms of physical connection may be omitted, the multi-purpose processing apparatus 10 being able to communicate with tablet PC 610 via wireless means.

It should be appreciated by the person skilled in the art that variations and modifications to the embodiments and adaptors mentioned above fall within the scope of the invention. In particular:

the "L" shaped arrangement of body 14 may be replaced with a "T"-shaped arrangement;

the shorter section 16 may be arranged such that, in normal orientation, it angles towards the operator;

there may be multiple interface connectors 30, 110;

The snap clips 112 and associated grooves 34 may be positioned at other locations.

Digital camera 36 may be replaced with a film-based camera, with means to digitise the film negative being used to allow the images taken to be stored or processed further by processing unit 602.

Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in this or related fields are intended to be within the scope of the following claims.

We claim:

1. A multi-purpose imaging apparatus comprising:
   a body; and
   imaging means housed within the body,
   wherein the body has a recessed portion adapted to releasably engage one of a plurality of adaptors, at least one of the adaptors has an aperture extending therethrough that aligns with the optical axis of the imaging means when so engaged such that at least a portion of the optical axis is not obscured,
   wherein the at least one adaptor has optics for illuminating a subject along the optical axis for a separate diagnostic purpose,
   wherein the optics comprise at least one light generating source positioned proximate the at least one adaptor,
   wherein the body has a first electrical contact and the at least one adaptor has a second electrical contact,
   wherein the first electrical contact is positioned on the body and the second electrical contact is positioned on the at least one adaptor such that when the at least one adaptor is releasably engaged with the body, the first electrical contact contacts the second electrical contact forming an electrical connection,
   wherein the at least one light generating source is powered via the electrical connection, and
   wherein a lens of the imaging means protrudes from a recessed face of the recessed portion, and when the at least one adaptor is releasably engaged with the body, a portion of the adaptor is located within the recessed portion and the lens of the imaging means is facing and in close proximity with the aperture of the at least on adaptor.

2. The multi-purpose imaging apparatus according to claim 1, wherein the imaging means is a digital camera.

3. The multi-purpose imaging apparatus according to claim 1, further comprising a removable memory means for storing images captured by imaging means.

4. The multi-purpose imaging apparatus according to claim 1, wherein the body is adapted to be carried in the hand.

5. An adaptor for the multi-purpose imaging apparatus according to claim 1, the adaptor comprising:
optics for illuminating a subject within the optical axis of the imaging means for diagnostic purposes;
means for releasably engaging the body; and
an aperture extending therethrough,
wherein, when releasably engaged with the body, the aperture aligns with the optical axis such that at least a portion of the optical axis of the imaging means is not obscured.

6. The adaptor according to claim 5, having optics arranged to function as a slit-lamp.

7. The adaptor according to claim 6, wherein the optics are arranged to include a first slit lamp device and a second slit lamp device.

8. The adaptor according to claim 6, wherein the optics includes a beam of light generated by at least one solid state lamp.

9. The adaptor according to claim 8, wherein the optics includes structures for defining a narrow slit, the beam of light being laterally trimmed by the narrow slit as it passes therethrough.

10. The adaptor according to claim 9, wherein the position of the structures may be adjusted to correspondingly adjust the width of the narrow slit.

11. The adaptor according to claim 9, wherein the width of the narrow slit is 0.08 mm.

12. The adaptor according to claim 9, wherein the optics further includes focusing means aligned with the narrow slit, the focusing means arranged to focus the laterally trimmed beam of light into a slit of light.

13. The adaptor according to claim 12, wherein the focusing means is a prism of uniform semi-circular cross-section.

14. The adaptor according to claim 6, wherein the optics further includes a light source for providing background illumination to the subject.

15. The adaptor according to claim 6, having optics arranged to image red reflex.

16. The adaptor according to claim 15, wherein the optics includes a beam-splitter received within the aperture and a light source positioned substantially at a right angle to the beam splitter.

17. The adaptor according to claim 16, wherein at least a portion of light split by the beam splitter is reflected along the optical axis of the imaging means.

18. The adaptor according to claim 17, having an additional aperture in the same plane as the light source for conveying at least some light not reflected by the beam splitter along the optical axis of the imaging means away from the optical axis of the imaging means.

19. The adaptor according to claim 6, having optics arranged to image the fluorescence of the subject.

20. The adaptor according to claim 19, wherein the optics includes at least one light source that generates a blue light.

21. The adaptor according to claim 20, wherein the optics includes a plurality of light sources that each generate a blue light, the plurality of light sources being disposed about the adaptor such that the subject is evenly illuminated by the blue light.

22. The adaptor according to claim 19, wherein the optics includes at least one yellow filter received within the aperture in the path of the optical axis of the imaging means.

23. The adaptor according to claim 6, having optics arranged to image tear-film.

24. The adaptor according to claim 6, having optics arranged to take a nibut image of the subject.

25. The adaptor according to claim 6, having optics arranged to capture dermatological images.

26. The adaptor according to any one of claims 23 through 25, wherein the optics includes a cylinder having open ends, a plurality of light sources being circumferentially disposed about one of the open ends.

27. The adaptor according to claim 26, wherein the light sources are light-emitting diodes.

28. The adaptor according to claim 26, wherein the disposition of the plurality of light sources is such that a homogenous light source is produced.

29. The adaptor according to claim 24, wherein the optics includes a cylinder having open ends, a plurality of light sources being circumferentially disposed about one of the open ends, and wherein the cylinder is transparent and the internal surface of the cylinder has a grid pattern printed thereon.

30. The adaptor according to claim 24, wherein the optics includes a cylinder having open ends, a plurality of light sources being circumferentially disposed about one of the open ends, and wherein the cylinder is adapted to receive about its internal surface a film having a grid pattern printed thereon.

31. The adaptor according to claim 25, wherein the optics further comprises a magnifying lens positioned such that it intersects the optical axis of the imaging means.

32. The adaptor according to claim 6, having optics arranged to function as a fundus camera.

33. The adaptor according to claim 32, wherein the optics includes a beam-splitter received within the aperture and a light source positioned substantially at a right angle to the beam splitter.

34. The adaptor according to claim 33, wherein at least a portion of light split by the beam splitter is reflected along the optical axis of the imaging means.

35. The adaptor according to claim 34, wherein light reflected along the optical axis of the imaging means is focused by a double convex lens to penetrate the iris and lens of a person's eye.

36. The adaptor according to claim 33, having an additional aperture in the same plane as the light source for conveying at least some light not reflected by the beam splitter along the optical axis of the imaging means away from the optical axis of the imaging means.

37. The adaptor according to claim 6, having optics arranged to capture dental images.

38. The adaptor according to claim 37, further comprising at least one angled aperture adapted to receive a dental mirror such that the mirror portion of the dental mirror intersects the optical axis of the imaging means.

39. The adaptor according to claim 38, wherein the adaptor has two angled apertures adapted to receive a dental mirror, the two angled apertures being disposed opposite one another relative to the aperture.

40. The adaptor according to claim 6, having optics arranged to function as an otoscope.

41. The adaptor according to claim 40, wherein the adaptor includes a removable ear plug.

42. The adaptor according to claim 41, wherein the removable ear plug has an opening at a tapered end, and the optics includes a light source that directs a beam of light through the opening to illuminate portions of the ear.

43. The adaptor according to claim 40, wherein the optics includes a lens intersecting the optical axis and focusing means for focusing the image viewable along the optical axis.

44. A multi-purpose imaging apparatus comprising:
a body;
imaging means housed within the body;
wherein the body has a recessed portion adapted to releasably engage one of a plurality of adaptors, at least one of the adaptors has an aperture extending therethrough that aligns with the optical axis of the imaging means when so engaged such that at least a portion of the optical axis is not obscured;
wherein the at least one adaptor has optics for illuminating a subject along the optical axis for a separate diagnostic purpose and wherein the optics comprise at least one light generating source positioned proximate the at least one adaptor;
user controls positioned on the body configured to allow the user to adjust optics and/or electrical operation of the at least one adaptor during use;
wherein the body has a first electrical contact and the at least one adaptor has a second electrical contact,
wherein the first electrical contact is positioned on the body and the second electrical contact is positioned on the at least one adaptor such that when the at least one adaptor is releasably engaged with the body, the first electrical contact contacts the second electrical contact forming an electrical connection,
wherein the at least one light generating source is powered via the electrical connection, and
a lens of the imaging means protrudes from a recessed face of the recessed portion, and when the at least one adaptor is releasably engaged with the body, a portion of the adaptor is located within the recessed portion and the lens of the imaging means is facing and in close proximity with the aperture of the at least on adaptor.

45. The multi-purpose imaging apparatus according to claim 44, wherein the imaging means is a digital camera.

46. A multi-purpose imaging apparatus according to claim 44, further comprising a removable memory means for storing images captured by imaging means.

47. A multi-purpose imaging apparatus according to claim 44, wherein the body is adapted to be carried in the hand.

48. An adaptor for a multi-purpose imaging apparatus according to claim 44, the adaptor comprising:
optics for illuminating a subject within the optical axis of the imaging means for diagnostic purposes;
means for releasably engaging the body; and
an aperture extending therethrough,
wherein, when releasably engaged with the body, the aperture aligns with the optical axis such that at least a portion of the optical axis of the imaging means is not obscured.

49. A multi-purpose imaging apparatus comprising:
a body; and
imaging means housed within the body,
wherein the body has a recessed portion adapted to releasably engage one of a plurality of adaptors, at least one of the adaptors has an aperture extending therethrough that aligns with the optical axis of the imaging means when so engaged such that at least a portion of the optical axis is not obscured,
wherein the at least one adaptor has optics for illuminating a subject along the optical axis for a separate diagnostic purpose,
wherein the optics comprise at least one light generating source positioned proximate the at least one adaptor,
wherein the body has a user control interface configured to allow a user to adjust the optics of the at least one adaptor when the at least one adaptor is releasably engaged with the body, wherein the adjustment includes controlling the brightness of the at least one light generating source, and
wherein a lens of the imaging means protrudes from a recessed face of the recessed portion, and when the at least one adaptor is releasably engaged with the body, a portion of the adaptor is located within the recessed portion and the lens of the imaging means is facing and in close proximity with the aperture of the at least on adaptor.

* * * * *